United States Patent
Jordan

(10) Patent No.: US 12,144,583 B2
(45) Date of Patent: Nov. 19, 2024

(54) DIFFUSION TENSOR MR TO MONITOR GLYMPHATIC SYSTEM

(71) Applicant: Synaptec Network, Inc, Santa Monica, CA (US)

(72) Inventor: Sheldon Jordan, Pacific Palisades, CA (US)

(73) Assignee: Synaptec Network, Inc., Santa Monica, CA (US)

( * ) Notice: Subject to any disclaimer, the term of this patent is extended or adjusted under 35 U.S.C. 154(b) by 352 days.

(21) Appl. No.: 16/824,718

(22) Filed: Mar. 20, 2020

(65) Prior Publication Data

US 2020/0297211 A1 Sep. 24, 2020

Related U.S. Application Data

(60) Provisional application No. 62/821,673, filed on Mar. 21, 2019.

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/4842* (2013.01);
(Continued)

(58) Field of Classification Search
CPC ..... A61B 5/0042; A61B 5/055; A61B 5/4809; A61B 5/4842; A61B 5/4848;
(Continued)

(56) References Cited

U.S. PATENT DOCUMENTS 9,681,821 B2 * 6/2017 Piron ................. A61B 5/4076
2003/0009098 A1 1/2003 Jack
(Continued)

FOREIGN PATENT DOCUMENTS

WO 03061466 7/2003
WO 2014130777 8/2014

OTHER PUBLICATIONS

David Bradshaw et al., "Nightly Sleep Duration in the 2-Week Period Preceding Multiple Sleep Latency Testing," Oct. 15, 2007, Journal of Clinical Sleep Medicine, vol. 3, No. 6, pp. 617 (Year: 2007).*

(Continued)

*Primary Examiner* — Joseph M Santos Rodriguez
*Assistant Examiner* — Maria Christina Talty
(74) *Attorney, Agent, or Firm* — Fish IP Law, LLP

(57) ABSTRACT

Systems and methods are contemplated for monitoring and analyzing the glymphatic system and brain to predict, prognose, diagnose, treat, modify or improve treatment, and track progression of neurological diseases. A first and second MRI image are taken of an extracellular space in a region of interest in a patient's brain, with one image taken while the patient is awake and the other image taken while the patient is asleep. The first and second images are compared to detect changes in the extracellular space, and the comparison is used to predict, prognose, diagnose, treat, modify or improve treatment, and track progression of neurological diseases associated with the extracellular space.

16 Claims, 2 Drawing Sheets

(51) Int. Cl.

| | | |
|---|---|---|
| *G01R 33/48* | (2006.01) | |
| *G01R 33/56* | (2006.01) | |
| *G06T 7/00* | (2017.01) | |
| *G16H 10/60* | (2018.01) | |
| *G16H 30/40* | (2018.01) | |
| *G16H 50/20* | (2018.01) | |
| *G16H 50/30* | (2018.01) | |
| *G16H 50/50* | (2018.01) | |

(52) U.S. Cl.
CPC ........ *A61B 5/4848* (2013.01); *G01R 33/4806* (2013.01); *G01R 33/5608* (2013.01); *G06T 7/0016* (2013.01); *G06T 7/97* (2017.01); *G16H 10/60* (2018.01); *G16H 30/40* (2018.01); *G16H 50/20* (2018.01); *G16H 50/30* (2018.01); *G16H 50/50* (2018.01); *G06T 2207/10088* (2013.01); *G06T 2207/30016* (2013.01)

(58) Field of Classification Search
CPC ............ G01R 33/4806; G01R 33/5608; G01R 33/56341; G06T 2207/10088; G06T 2207/10092; G06T 2207/30016; G06T 7/0016; G06T 7/97; G16H 10/60; G16H 30/40; G16H 50/20; G16H 50/30; G16H 50/50

See application file for complete search history.

(56) References Cited

U.S. PATENT DOCUMENTS

| | | | | |
|---|---|---|---|---|
| 2009/0024181 | A1* | 1/2009 | Raghavan | A61B 6/501 607/45 |
| 2013/0324831 | A1 | 12/2013 | Hundley | |
| 2015/0073260 | A1* | 3/2015 | Yang | G01R 33/56308 600/411 |
| 2016/0367166 | A1 | 12/2016 | Piron | |
| 2017/0079581 | A1* | 3/2017 | Walczak | A61K 47/26 |
| 2018/0268942 | A1 | 9/2018 | Kamali-Zare | |

OTHER PUBLICATIONS

Arie Oksenberg et al., "Positional vs Nonpositional Obstructive Sleep Apnea Patients: Anthropomorphic, Nocturnal Polysomnographic and Multiple Sleep Latency Test Data," Sep. 1997, Clinical Investigations: Sleep and Breathing, vol. 112, Issue 3, pp. 633 (Year: 1997).*

Nina Hofle, et al., "Regional Cerebral Blood Flow Changes as a Function of Delta and Spindle Activity during Slow Wave Sleep in Humans," Jun. 15, 1997, The Journal of Neuroscience vol. 12, Issue 12, pp. 4800-4808 (Year: 1997).*

P. Guldenmund et al., "Brain functional connectivity differentiates dexmedetomidine from propofol and natural sleep," Oct. 2017, British Journal of Anaesthesia, vol. 119, Issue 4, pp. 674-684 (Year: 2017).*

Jessen, Nadia Aalling; et al. "The Glymphatic System—A Beginner's Guide," Neurochem Res. Dec. 2015 ; 40 (12): 2583-2599.

Melhem ER, Mori S, Mukundan G, Kraut MA, Pomper MG, van Zijl PC. Diffusion tensor MR imaging of the brain and white matter tractography. AJR Am J Roentgenol. 2002;178(1):3-16. doi:10.2214/ajr.178.1.1780003.

Plog, Benjamin A, and Maiken Nedergaard. "The Glymphatic System in Central Nervous System Health and Disease: Past, Present, and Future." Annual review of pathology vol. 13 (2018): 379-394. doi:10.1146/annurev-pathol-051217-111018.

Taoka, Toshiaki; et al. "Evaluation of glymphatic system activity with the diffusion MR technique: diffusion tensor image analysis along the perivascular space (DTI-ALPS) in Alzheimer's disease cases," Japanese Journal of Radiology. Feb. 2017. pp. 1-27.

Zhang H, Schneider T, Wheeler-Kingshott CA, Alexander DC. NODDI: practical in vivo neurite orientation dispersion and density imaging of the human brain. Neuroimage. 2012;61(4):1000-1016. doi:10.1016/j.neuroimage.2012.03.072.

International search report dated Dec. 9, 2020, for related PCT application No. PCT/US2020/023740, filed on May 20, 2020. 16 pages.

* cited by examiner

DIFFUSION TENSOR MR TO MONITOR GLYMPHATIC SYSTEM

This application claims priority to U.S. provisional application 62/821,673, filed Mar. 21, 2019, the disclosure of which is incorporated herein by reference.

FIELD OF THE INVENTION

The field of the invention is methods, systems, kits, and devices related to monitoring the brain.

BACKGROUND

The background description includes information that may be useful in understanding the present invention. It is not an admission that any of the information provided herein is prior art or relevant to the presently claimed invention, or that any publication specifically or implicitly referenced is prior art.

The recently discovered glymphatic system has drawn interest and investigation into the system's implications and impacts on neurological diseases. Indeed, Evaluation Of Glymphatic System Activity With The Diffusion MR Technique: Diffusion Tensor Image Analysis Along The Perivascular Space (DTI-ALPS) In Alzheimer's Disease Cases, Japanese Journal of Radiology (February 2017) by Nagoya Taoka, et al, teaches Diffusion Tensor Imaging (DTI) can be used to detect the diffusivity of water in the perivascular space of the human brain. Taoka further teaches that such diffusivity can be correlated to mini mental state examination scores and Alzheimer's Disease (AD) severity to relate states of the glymphatic system with AD. However, Taoka merely scratches the surface of potential applications borne from monitoring or analyzing the glymphatic system, and fails to provide therapeutic specifics.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Further study of the glymphatic system's role in removing waste materials from vertebrate central nervous systems has led to attempts to use the glymphatic system as a barometer for neurological health. For example, U.S. Pat. No. 9,681,821 to Piron et al teaches using DTI to detect perfusion and flow of cerebrospinal fluid, specifically measuring the draining of interstitial fluid and extracellular fluid during a patient's sleep state to indicate neurological pathology. While Piron teaches using DTI to quantify glymphatic flow in both awake and sleep states of a patient, Piron does not provide detection methods with sufficient image resolution or quantification of fluids in the intracellular space versus the extracellular space of patients or of free water. Likewise, Piron does not provide for temporally proximal detection and analysis of awake and sleep states of a patient.

Thus, there remains a need for systems and methods for increased resolution and quantification of intracellular space and extracellular space in a patient's brain and glymphatic system for various clinical or therapeutic uses, as well as methods providing direct and temporally proximal detection and analysis of a patient's glymphatic system and brain in sleep and awake states.

SUMMARY OF THE INVENTION

The inventive subject matter provides apparatus, systems, and methods for monitoring and analyzing the glymphatic system and brain to predict, prognose, diagnose, treat, modify or improve treatment, and track progression of neurological diseases. Contemplated methods include analyzing an extracellular space in a region of interest (ROI) in a patient's brain. A first image and a second image are taken of the ROI via magnetic resonance imaging (MRI) (preferably diffusion tensor imaging (DTI), and more preferably neurite orientation dispersion and diffusion imaging (NODDI)). The first and second images are compared to detect changes in the extracellular space in the ROI. In preferred embodiments, the first image is taken while the patient is awake and the second image is taken while the patient is asleep, or vice versa.

Further methods include monitoring a change in a patient's glymphatic system. A first and a second image are taken of a region of the patient's glymphatic system via NODDI, with the first image preferably taken while the patient is awake and the second image taken while the patient is asleep, or vice versa. The first image is then compared with the second image to monitor or detect changes in the region of the patient's glymphatic system. The first and second images are typically taken less than 30 minutes apart, preferably less than 10, 5, or 3 minutes apart, with the second image taken while the patient is in artificially induced sleep, preferably slow-wave sleep.

Methods of diagnosing a patient with a neurodegenerative disease include monitoring a change in an extracellular space in a patient's glymphatic system between an awake state and a temporally proximal sleep state of the patient, preferably using NODDI to monitor the change in the extracellular space, with the awake state and the temporally proximal sleep state separated by less than 10 minutes, preferably less than 5 minutes. Alternatively or in combination, methods of diagnosing a patient with a disease also include monitoring a change in free water in an extracellular space of a patient's glymphatic system between an awake state and a temporally proximal sleep state of the patient.

Methods of tracking disease progression in a patient with a disease contemplate monitoring a change in an extracellular space in a patient's glymphatic system between an awake state and a temporally proximal sleep state of the patient, and comparing the change in the extracellular space with a previous record of the extracellular space form the patient.

Methods of predicting a disease prognosis in a patient with a disease further contemplate monitoring a change in an extracellular space in a patient's glymphatic system between an awake state and a temporally proximal sleep state of the patient, and comparing the change with a previous extracellular space record from the patient to predict the disease prognosis.

Methods of predicting a response of a patient to a treatment include monitoring a change in an extracellular space in a patient's glymphatic system between an awake state and a temporally proximal sleep state of the patient, and comparing the change with a previous extracellular space record from the patient to predict the response of the patient.

Methods of targeting treatment in a patient with a disease contemplate monitoring a change in an extracellular space in a patient's glymphatic system between an awake state and a temporally proximal sleep state of the patient, and using the change in the extracellular space to target regions for treatment or types of treatment suited for the change in the extracellular space.

DETAILED DESCRIPTION

Figure 1:
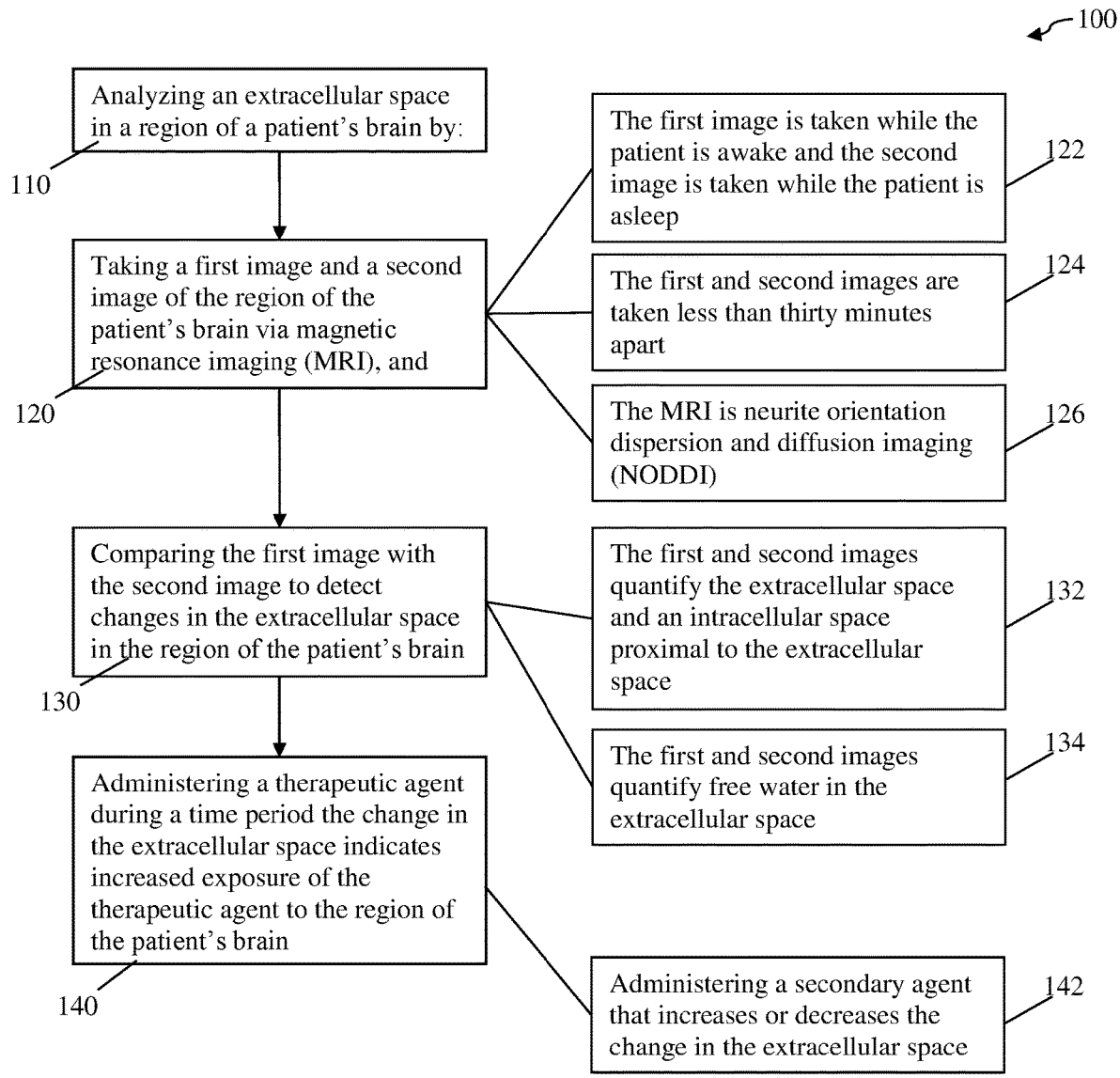
FIG. 1 depicts a flow chart of a method of the inventive subject matter.

The inventive subject matter provides apparatus, systems, and methods for monitoring and analyzing the glymphatic system and brain to predict, prognose, diagnose, treat, modify or improve treatment, and track progression of neurological diseases. Contemplated methods include analyzing an extracellular space in a region of interest (ROI) in a patient's brain. A first image and a second image are taken of the ROI via magnetic resonance imaging (MRI) (preferably diffusion tensor imaging (DTI), and more preferably neurite orientation dispersion and diffusion imaging (NODDI)). The first and second images are compared to detect changes in the extracellular space in the ROI. In preferred embodiments, the first image is taken while the patient is awake and the second image is taken while the patient is asleep, or vice versa.

The first and second images are taken less than thirty minutes apart, preferably less than 10, 5, or 3 minutes apart. An image, whether first or second, is preferably taken while the patient is in slow-wave sleep. Comparing temporally proximal awake and asleep states of the glymphatic system is critical in some embodiments, as the elasticity or responsiveness of the glymphatic system can indicate neurological pathology or disease progression. As such, the second image is taken after the patient is artificially induced into sleep in some embodiments, for example through administration of dexmedetomidine or other anesthetic appropriate to induce slow-wave sleep.

The first and second images typically quantify the extracellular space and an intracellular space proximal (e.g., within 1 cm, 2 cm, 3 cm, 4 cm, etc.) to the extracellular space, though it is contemplated that the first and second images alternatively, or in combination, quantify free water in the extracellular space.

Uses for the inventive methods are contemplated, for example (i) to assess a condition of the patient's glymphatic system (e.g., compare awake and asleep NODDI of extracellular versus intracellular space or free water), (ii) to diagnose a condition of the patient's glymphatic system (e.g., comparing awake or sleep, or both, NODDI of extracellular versus intracellular space or free water with normalized peer disease positive standards), (iii) to prognose a disease condition (e.g., comparing awake or sleep, or both, NODDI of extracellular versus intracellular space or free water with normalized peer samples with treatment positive or treatment negative response), (iv) to compose effective therapies (e.g., compare awake or sleep, or both, NODDI of extracellular versus intracellular space or free water to identify regions suitable for treatment or indications of treatment positive response), (v) to track disease or treatment progress (e.g., compare awake or sleep, or both, NODDI of extracellular versus intracellular space or free water with prior recordings or normalized peer standards), or (vi) to modify or improve a therapeutic regimen (e.g., compare past and current awake or asleep, or both, NODDI of each of extracellular or intracellular spaces or free water, or comparisons between extracellular and intracellular spaces or free water, with disease progressive or disease remission NODDI associated with a treatment protocol or series of treatment protocols to alter or improve therapeutic regimen).

Further methods include monitoring a change in a patient's glymphatic system. A first and a second image are taken of a region of the patient's glymphatic system via NODDI, with the first image preferably taken while the patient is awake and the second image taken while the patient is asleep, or vice versa. The first image is then compared with the second image to monitor or detect changes in the region of the patient's glymphatic system. The first and second images are typically taken less than 30 minutes apart, preferably less than 10, 5, or 3 minutes apart, with the second image taken while the patient is in artificially induced sleep, preferably slow-wave sleep.

The first and second images typically quantify (i) an extracellular space in the region of the patient's glymphatic system and (ii) an intracellular space proximal (e.g., adjacent, within 1 cm, 2 cm, 3 cm, 4 cm, etc) to the extracellular space. Alternatively or in combination, the first and second images quantify free water in an extracellular space in the region of the patient's glymphatic system.

Methods of diagnosing a patient with a neurodegenerative disease include monitoring a change in an extracellular space in a patient's glymphatic system between an awake state and a temporally proximal sleep state of the patient, preferably using NODDI to monitor the change in the extracellular space, with the awake state and the temporally proximal sleep state separated by less than 10 minutes, preferably less than 5 minutes. Alternatively or in combination, methods of diagnosing a patient with a disease also include monitoring a change in free water in an extracellular space of a patient's glymphatic system between an awake state and a temporally proximal sleep state of the patient.

Methods of tracking disease progression in a patient with a disease contemplate monitoring a change in an extracellular space in a patient's glymphatic system between an awake state and a temporally proximal sleep state of the patient, and comparing the change in the extracellular space with a previous record of the extracellular space form the patient.

Methods of predicting a disease prognosis in a patient with a disease further contemplate monitoring a change in an extracellular space in a patient's glymphatic system between an awake state and a temporally proximal sleep state of the patient, and comparing the change with a previous extracellular space record from the patient to predict the disease prognosis.

Methods of predicting a response of a patient to a treatment include monitoring a change in an extracellular space in a patient's glymphatic system between an awake state and a temporally proximal sleep state of the patient, and comparing the change with a previous extracellular space record from the patient to predict the response of the patient.

Methods of targeting treatment in a patient with a disease contemplate monitoring a change in an extracellular space in a patient's glymphatic system between an awake state and a temporally proximal sleep state of the patient, and using the change in the extracellular space to target regions for treatment or types of treatment suited for the change in the extracellular space.

It is contemplated that analysis of extracellular space versus intracellular space, free water, or extracellular fluid versus intracellular fluid includes a voxel by voxel comparison between patient awake state images (e.g., via NODDI) and patient asleep state images (e.g., slow-wave induced sleep). Ratios can be derived between the various metrics. For example, a ratio of extracellular space to intracellular space (or extracellular and intracellular free water, or extracellular fluid to intracellular fluid, etc.) can be calculated for the awake state and the asleep state (e.g., awake ratio and asleep ratio).

While deviations between a patient's awake ratio over a period of time or in comparison to normalized peer standards may indicate neurological health or disease potential, deviations between the asleep ratio over time or compared to normalized standard are surprisingly strong indications of the presence or progress of a neurological disease state in a patient. For example, where ratios of extracellular space to intracellular space (or fluid, or free water, or combinations thereof) in the asleep state are lower (e.g., 10% lower, 20% lower, 30% lower, 40% lower, more than 50% lower), there is a strong indication that the glymphatic system is not properly functioning, and a neurological disease condition may exist in the patient or may be progressing.

Additional analysis of the various metrics detected or monitored in the inventive subject matter offer further improvements to monitoring, diagnosing, prognosing, treating, or designing treatment for a disease condition. A ratio of the extracellular space (or free water, or fluid, or combinations thereof) of the awake and the sleep state can be calculated, with a ratio of awake:sleep above a peer standardized baseline indicative of a disease state or disease progression, while a ratio of awake:sleep below a peer standardized baseline indicative of a reduced disease state, treatment positive effect, or otherwise healthy neurological condition. Likewise, comparison of a patient's awake:sleep ratio measured over time can indicate treatment positive effect (decrease in ratio), disease progression (increase in ratio), or ineffective treatment (marginal change in ratio, increase in ratio, etc.).

A ratio of the intracellular space (or free water, or fluid, or combinations thereof) of the awake and the sleep state can also be calculated and used in combination or apart from other ratios discussed. For example, a ratio of awake:sleep intracellular space (or free water, or fluid, or combinations thereof) above a peer standardized baseline can indicate a reduced disease state, treatment positive effect, or otherwise healthy neurological condition, while a ratio of awake:sleep below a peer standardized baseline can indicate a disease state or disease progression. Likewise, comparison of a patient's awake:sleep ratio measured over time can indicate treatment positive effect (increase in ratio), disease progression (decrease in ratio), or ineffective treatment (marginal change in ratio, decrease in ratio, etc).

The methods and systems of the inventive subject matter can be applied to detect or monitor various states of the glymphatic system with various related clinical, therapeutic, or disease indications. For example, indications of Mild Cognitive Impairment, Alzheimer's Disease, Frontotemporal Dementia, Parkinson's Disease and related Dementias, Vascuar Dementia, Stroke, Traumatic Brain Injury, Postconcussive Syndrome, Diabetes, Encephalopathy, Sleep Disorders, and Mood Disorders that affect sleep (e.g. anxiety, depression, etc.), are detectable by the inventive subject matter, and can be used for early prediction of a disease state, as a prognostic indicator, tracking or monitoring a disease state, guiding treatment, or otherwise tracking treatment progress. Table 1 below provides a summary of a number of variables that can be detected, quantified, and monitored by methods and systems of the inventive subject matter.

TABLE 1

| Variables | Metrics (applied to Variables A-I) |
|---|---|
| A) Extracellular Space Value | 1) Awake To Asleep Ratio* |
| B) Intracellular Space Value | 2) Awake to Asleep Difference (i.e. subtraction method)* |
| C) Total Cellular Volume Value | 3) Awake to Asleep Ratio compared to Normative Group* |
| D) Free Water Value | 4) Awake to Asleep Difference Compared to Normative Group* |
| E) Total Available Water Value | 5) Awake to Asleep Difference Related to Likelihood of Disease State (e.g. Machine Learning Diagnostic Prediction)* |
| F) Ratio of Extracellular to Intracellular Space Value | 6) Change in Awake to Asleep Ratio over Time** |
| G) Ratio of Extracellular to Total Cellular Value | 7) Change in Awake to Asleep Difference over Time** |
| H) Ratio of Intracellular to Total Cellular Volume Value | |
| I) Ratio of Free Water to Total Available Water Value | |

*Any of metrics 1-5 can be used to target delivered therapies or predict targeted therapy success (e.g. exosomes, drug delivery)
**Any of 6-7 can be used to monitor delivered therapies over time and predict improvements in therapy success Each of the variables are measurable at an awake state, a sleep state, a natural or induced transition from awake to sleep state, or a natural or induced transition from sleep to awake state, for example single instances, over a period of time (e.g., continuous monitoring or periodic instances), or averaged over a period of time (e.g., from continuous monitoring or periodic instances). Likewise, the variables can be monitored before, during, and after a therapeutic has been administered to a patient in order to monitor or evaluate the effect or efficacy of the therapeutic on the glymphatic system.

Surprisingly, the inventive subject matter can also be applied to improve delivery or therapeutic agents to the brain. For example, for therapeutic agents delivered through cerebrospinal fluid with targets in the brain, an increase in the extracellular space, volume, or fluid favorably increases exposure of such therapeutic agents to targets in the brain. The inventive subject matter can be applied to track increases extracellular space in ROI of the glymphatic system to optimally time and condition administration or therapeutic agents. Further, the inventive subject matter can identify secondary agents that increase extracellular space in a regionally specific manner. Such secondary agents can be favorably administered in conjunction with therapeutic agents to preferentially improve delivery of the therapeutic agent to the targeted region of the brain. Likewise, secondary agents can also be identified with the inventive subject matter that decrease the extracellular space in specific regions. Such secondary agents can then be applied to reduce delivery of therapeutic agents to areas of the brain that trigger undesirable side effects or other adverse effects.

FIG. 1 depicts flow chart 100 for a method of the inventive subject matter, with steps 110, 120, and 130, along with optional or preferred steps 122, 124, 126, 132, and 134 as described therein.

Figure 2:
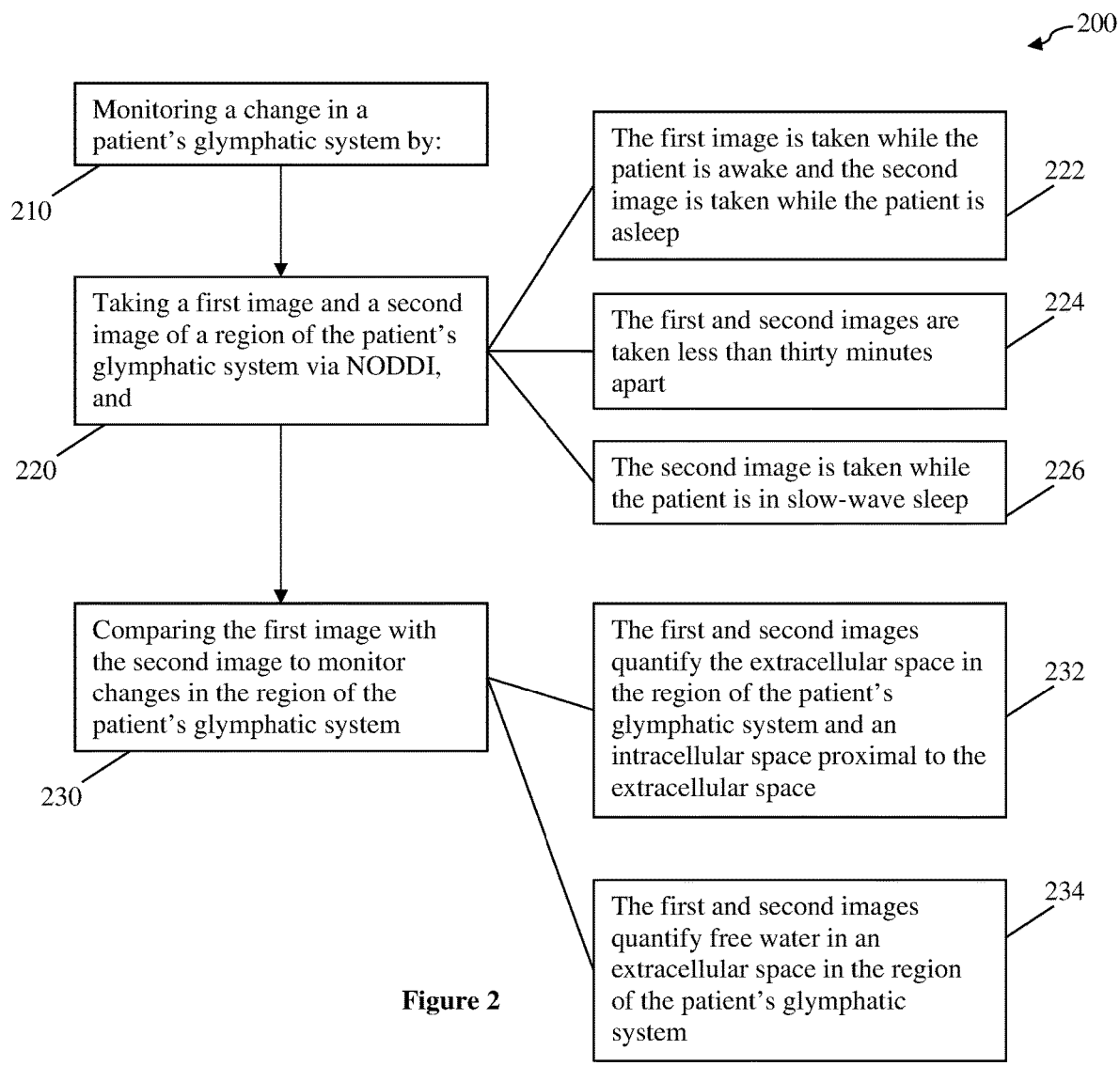
FIG. 2 depicts a flow chart of another method of the inventive subject matter.

FIG. 2 depicts flow chart 200 for a method of the inventive subject matter, with steps 210, 220, and 230, along with optional or preferred steps 222, 224, 226, 232, and 234 as described therein.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Various objects, features, aspects, and advantages of the inventive subject matter will become more apparent from the following detailed description of preferred embodiments, along with the accompanying drawing figures in which like numerals represent like components.

The inventive subject matter provides apparatus, systems, and methods for comparative analysis of tissue and organ scans between patients or groups of patients without sensitivity to patient-specific or scanner specific characteristics, including prediction, diagnosis, prognosis, tracking, and treatment guidance.

The following description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a neurological disease in a region of a patient's brain, comprising:
    taking a first image and a second image of the region of the patient's brain via magnetic resonance imaging (MRI);
    comparing the first image with the second image to detect a change in an extracellular space in the region of the patient's brain;
    administering a therapeutic agent responsive to the neurological disease when, during a time period, the change in the extracellular space indicates increased exposure of the therapeutic agent to the region of the patient's brain; and
    administering a secondary agent that increases or decreases the change in the extracellular space;
    wherein the first image is taken while the patient is awake, the second image is taken while the patient is asleep, and the first and second images are taken less than thirty minutes apart.

2. The method of claim 1, wherein the MRI is diffusion tensor imaging (DTI).

3. The method of claim 2, wherein the first and second images quantify the extracellular space and an intracellular space proximal to the extracellular space.

4. The method of claim 2, wherein the first and second images quantify free water in the extracellular space.

5. The method of claim 1, wherein the first and second images are taken less than ten minutes apart.

6. The method of claim 1, wherein the second image is taken while the patient is in slow-wave sleep.

7. The method of claim 1, wherein the second image is taken after the patient is artificially induced into sleep.

8. The method of claim 7, wherein the patient is artificially induced into sleep using dexmedetomidine.

9. Use of the method of claim 1 to assess a condition of the patient's glymphatic system.

10. The method of claim 1, wherein the change is an increase in extracellular space in the region of the patient's brain.

11. The method of claim 10, wherein the secondary agent increases the change to thereby improve delivery of the therapeutic agent to the region of the patient's brain.

12. The method of claim 10, wherein the secondary agent decreases the change to thereby reduce delivery of the therapeutic agent to the region of the patient's brain.

13. The method of claim 1, wherein the first and second images are taken less than five minutes apart.

14. The method of claim 1, wherein the first and second images are taken less than ten minutes apart and the second image is taken after the patient is artificially induced into sleep.

15. The method of claim 1, wherein the secondary agent is administered in conjunction with the therapeutic agent.

16. The method of claim 1, wherein the therapeutic agent is delivered via cerebrospinal fluid.

* * * * *